US008579916B2

(12) United States Patent
Cheney

(10) Patent No.: US 8,579,916 B2
(45) Date of Patent: Nov. 12, 2013

(54) THERMAL SEPARATION OF IMPURITIES FROM THE SCALP, HAIR, AND SKIN

(76) Inventor: Sharon Ann Cheney, Barrington, NH (US)

(*) Notice: Subject to any disclaimer, the term of this patent is extended or adjusted under 35 U.S.C. 154(b) by 1748 days.

(21) Appl. No.: 11/391,821

(22) Filed: Mar. 30, 2006

(65) Prior Publication Data

US 2007/0043382 A1     Feb. 22, 2007

Related U.S. Application Data

(60) Provisional application No. 60/708,952, filed on Aug. 18, 2005.

(51) Int. Cl.
    A61B 17/50    (2006.01)

(52) U.S. Cl.
    USPC .......................................................... 606/131

(58) Field of Classification Search
    USPC .............................. 606/131, 132, 9; 514/880;
                    604/289–291, 313, 315; 601/12, 16,
                                                601/17; 132/200
    See application file for complete search history.

(56) References Cited

U.S. PATENT DOCUMENTS

| 4,292,971 | A |   | 10/1981 | Smit et al. |       |
|-----------|---|---|---------|-------------|-------|
| 4,469,092 | A |   | 9/1984  | Marshall    |       |
| 4,765,316 | A |   | 8/1988  | Marshall    |       |
| 4,836,192 | A |   | 6/1989  | Abbate      |       |
| 5,228,431 | A |   | 7/1993  | Giarretto   |       |
| 5,454,778 | A |   | 10/1995 | Liaskos     |       |
| 6,086,682 | A |   | 7/2000  | Anderson    |       |
| 6,139,553 | A | * | 10/2000 | Dotan       | 606/131 |
| 6,162,232 | A | * | 12/2000 | Shadduck    | 606/131 |
| 6,273,884 | B1|   | 8/2001  | Altshuler   |       |
| 6,423,078 | B1| * | 7/2002  | Bays et al. | 606/131 |
| 6,726,693 | B2|   | 4/2004  | Weber       |       |
| 6,764,493 | B1| * | 7/2004  | Weber et al.| 606/131 |
| 7,318,828 | B1| * | 1/2008  | Revivo      | 606/131 |
| 2001/0023351 | A1 | * | 9/2001 | Eilers et al. | 606/131 |
| 2002/0183811 | A1 | * | 12/2002 | Irwin      | 607/94 |
| 2005/0075651 | A1 | * | 4/2005 | Ortiz       | 606/131 |

* cited by examiner

Primary Examiner — Thomas McEvoy
Assistant Examiner — Jocelin Tanner
(74) Attorney, Agent, or Firm — Zip Law PLLC; Claire Zopf

(57) ABSTRACT

Presented is a simple, novel, process of removing impurities from the scalp, hair, and skin. The process consists of, simultaneously, freezing the impurities with dry, chilled air, freeing the frozen impurities by abrading, and removing the frozen impurities by vacuum suctioning.

7 Claims, 5 Drawing Sheets

Figure 1 - Side View
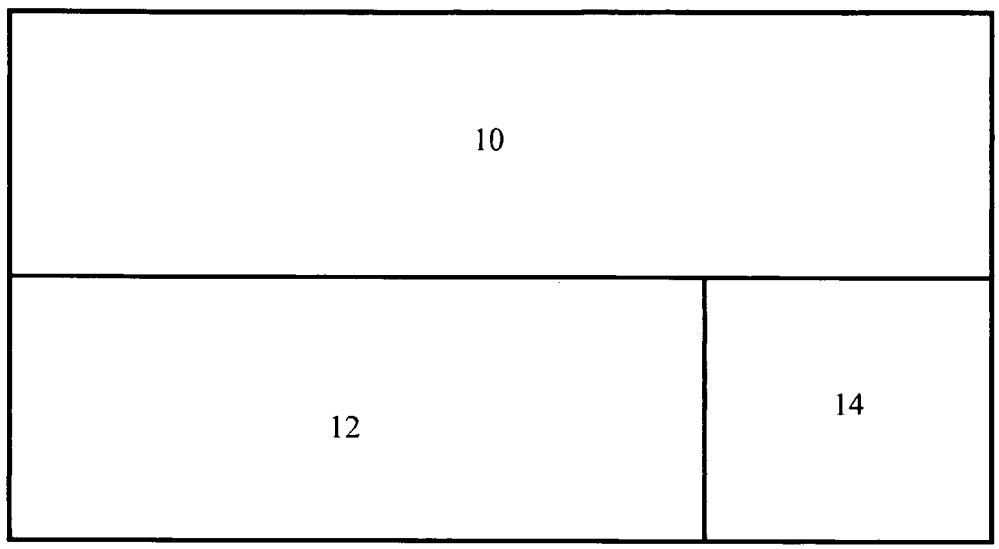
Figure 1A - Front View
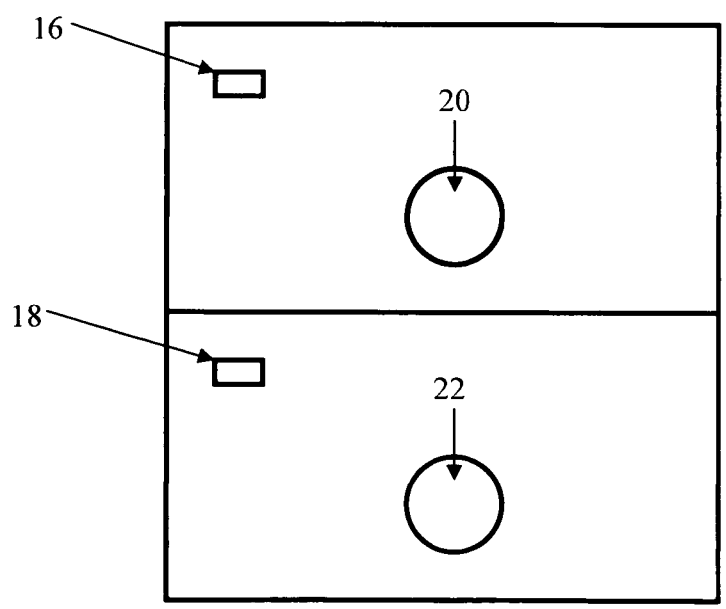

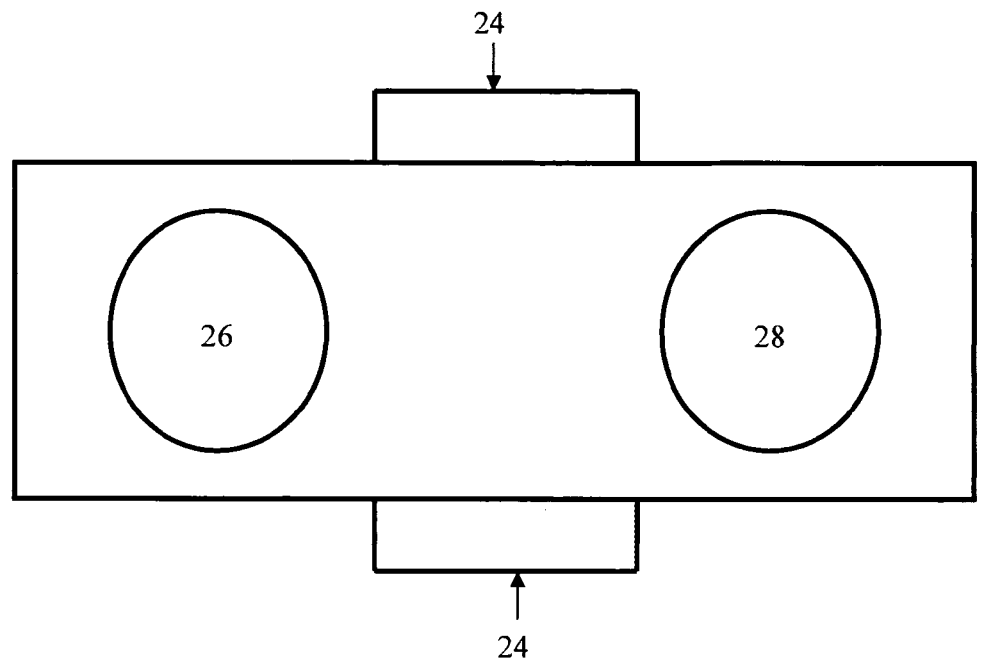
Figure 2 - Top View
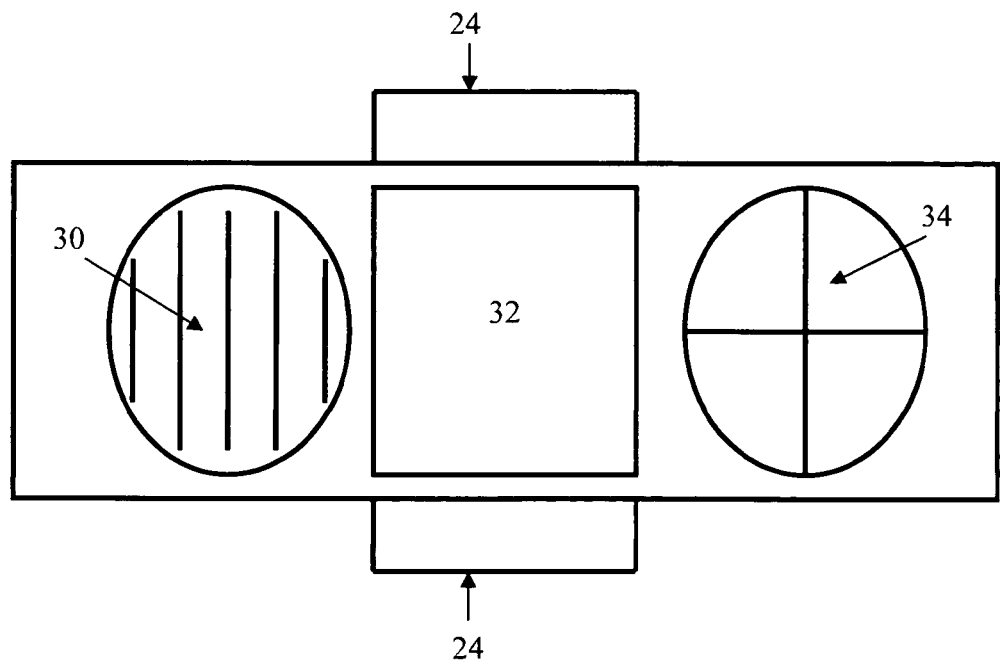
Figure 2A - Bottom View

Figure 3 - Top View
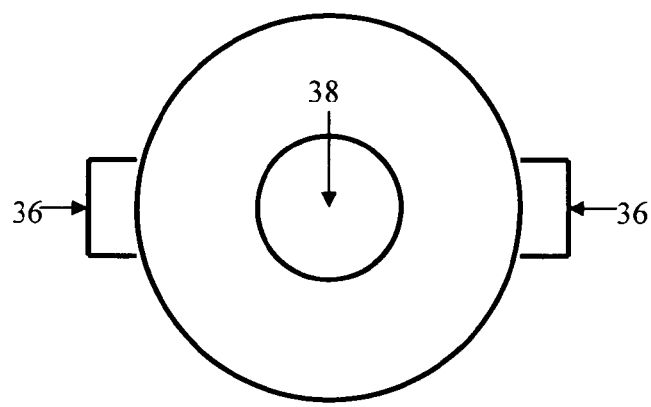
Figure 3A - Bottom View
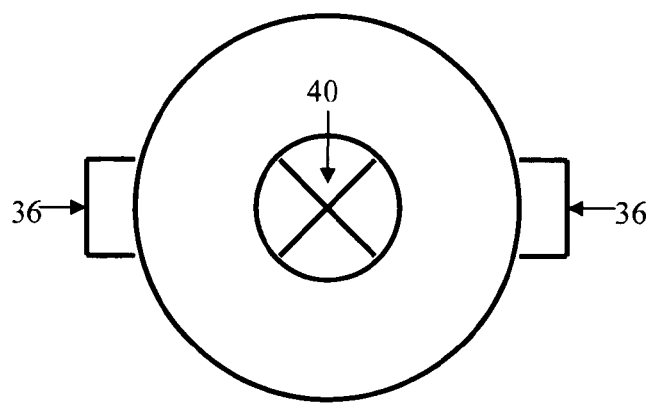

Figure 4 - Front View
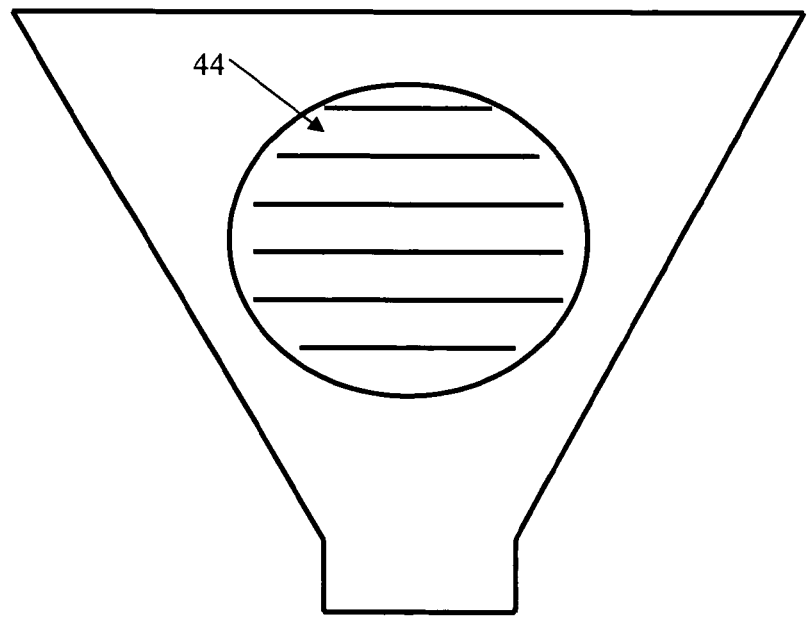
Figure 4A - Back View
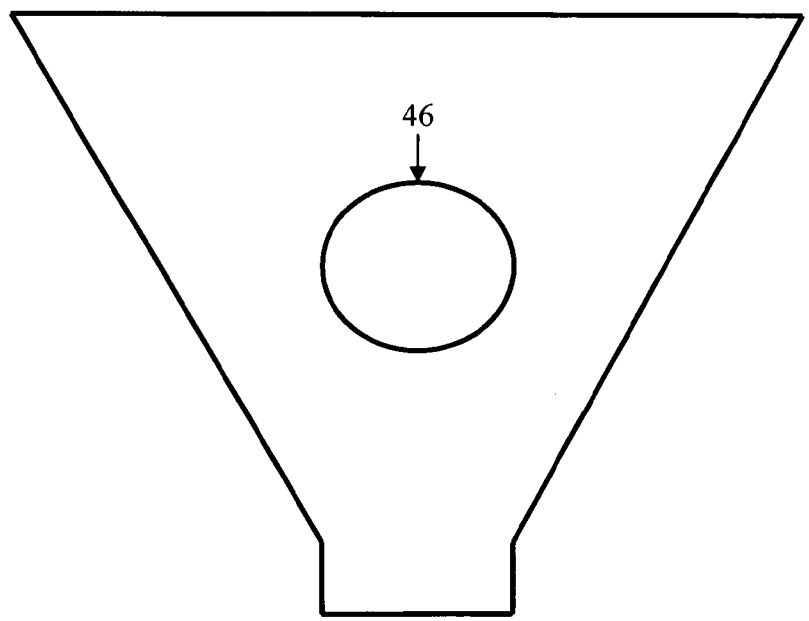

THERMAL SEPARATION OF IMPURITIES FROM THE SCALP, HAIR, AND SKIN

CROSS REFERENCE TO RELATED APPLICATIONS

Previously filed under provisional patent application No. 60/708,952, filed 2005 Aug. 18.

BACKGROUND

1. Field of Invention

This invention relates to the field of improving the appearance and health of the human scalp, hair, and skin; more specifically a treatment of separating, freeing, and removing impurities from their surfaces.

2. Description of Prior Art

Many techniques have been employed for the purpose of improving the appearance and health of the human scalp, hair, and skin. Scalp and skin treatments include topical applications, exfoliation treatments, chemical peels, use of abrading tools, microdermabrasion (particles are propelled at the skin), blood circulation stimulation devices, and laser treatments to name a few.

Applying a uniquely formulated topical on the scalp, hair, or skin is one method of improving health and quality. Topicals generally require a daily or twice daily application for the rest of one's life to achieve and maintain maximum results. The dangers of allergic or sensitivity reactions are present with topical use. Topicals, particularly those intended for hair rejuvenation, produce little or no improvement for much of the population. Improvements achieved from topicals are generally lost when the product's use is discontinued. Specially formulated topicals are costly.

Vacuum suction is used, in combination with an attached comb or brush, to remove impurities such as dandruff or parasites and their eggs from the scalp and hair. Although these tools may remove dandruff and parasites, removal may be limited to surface impurities. Impurities bonded to the scalp generally remain undisturbed.

Abrading tools are used to scrape the surfaces of the scalp, hair, or skin to loosen surface debris. Abrading tools do not differentiate between impurities and healthy tissue. With no attempt to alter the physical or chemical properties of the impurities, its bond with healthy skin tissue remains intact. Healthy tissues are regarded, therefore abraded, in the same manner as the impurities. Abrading tools requiring a specially formulated topical, for use in conjunction with its use, inherit problems associated with topicals.

Microdermabrasion is used for skin resurfacing. This technique allows the same insult to healthy skin tissue as mentioned for abrading tools. Anesthetics may be needed for pain relief during treatment. These procedures are costly and must be administered by a trained professional.

Stimulating blood circulation, in the surface areas of the scalp or skin, is used to improve their health. Helmet devices, designed for scalp applications, use a vacuum suction function to change the atmospheric pressure within the helmet to stimulate blood circulation. Many are designed to open skin pores or hair follicles for impurity expulsion. Many use a heat source to encourage impurity softening along with bodily perspiration as a method of altering the physical state of the impurities. Actual impurity removal appears inadequate due to the "wet" nature of the impurities. Many of these devices require multiple steps to achieve the maximum results.

Many methods are in place which requires the use of trained professionals. These techniques include, but are not limited to, chemical peels, laser treatments, and surgeries. These methods can be painful with the potential to present greater health and injury risks. Procedures are costly to the consumer and many require follow up procedures to achieve or maintain maximum results.

OBJECTS AND ADVANTAGES

Accordingly, several objects and advantages of my invention are:

(a) its simplicity in theory and in its operation;
(b) to provide a novel and thorough means of removing impurities from the scalp, hair, and skin;
(c) to provide a process which requires no messy clean up;
(d) to provide a relatively inexpensive process to employ;
(e) to provide a process which does not require specialized topicals, therefore, minimizing the event of an adverse health reaction;
(f) to provide a process which can be performed safely in the privacy of one's home;
(g) to provide a process that is virtually painless; a process which may even feel pleasant to the recipient;
(h) to provide a process that can be performed as frequently or infrequently as one chooses;
(i) to provide a process, when administered correctly, that exhibits minimal reversal of previous effects achieved.

DRAWING FIGURES

FIG. 1 shows the side view of the preferred embodiment of a "chilled air and vacuum suction unit".

FIG. 1A shows the front view of FIG. 1.

FIG. 2 shows the top view of the preferred embodiment of a hand held "scalp, hair, and skin, treatment tool".

FIG. 2A shows the bottom view of FIG. 2.

FIG. 3 shows the top view of the preferred embodiment of a hand held "facial skin treatment tool".

FIG. 3A shows the bottom view of FIG. 3.

FIG. 4 shows the front view of the preferred embodiment of a "chilled air flow funnel".

FIG. 4A shows the back view of FIG. 4.

---

Figure 5:
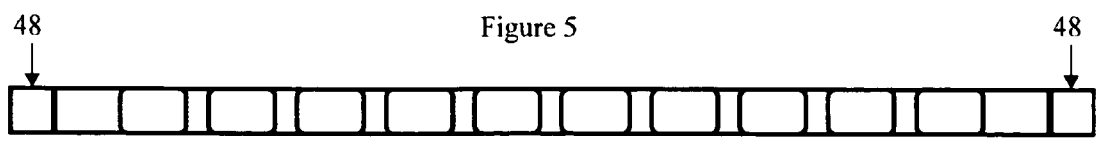
FIG. 5 shows the preferred embodiment of a "chilled air connective hose".

Reference Numerals in Drawings 10 chilled air source
12 vacuum suction source
14 waste collection location
16 chilled air source power switch
18 vacuum suction source power switch
20 chilled air source connective hose port
22 vacuum suction source connective hose port
24 abrading platform pulse power switch
26 chilled air connective hose port
28 vacuum suction connective hose port
30 chilled air exhaust vent
32 abrading accessory attachment platform
34 vacuum suction cavity
36 abrading platform pulse power switch
38 vacuum suction connective hose port
40 vacuum suction cavity
42 abrading accessory attachment platform
44 chilled air exhaust vent -continued

| Reference Numerals in Drawings |
| --- |
| 46 chilled air connective hose port |
| 48 chilled air hose connections |
| 50 vacuum suction hose connections |

SUMMARY

This invention utilizes a process which substantially decreases impurities' attraction for the scalp, hair, and skin, permitting a more thorough impurity extraction.

DESCRIPTION

FIGS. 1 to 6

FIG. 1 shows the side view of a "chilled air and vacuum suction unit". The top component is a "chilled air source" 10 capable of delivering and maintaining a "dry" air flow temperature of approximately 7° C. The bottom components consist of a "vacuum suction source" 12 capable of administering suction capability similar to an average household vacuum. The third component, positioned behind the vacuum source, is reserved for a "waste collection location" 14.

FIG. 1A is a front view of the FIG. 1 unit. The front view displays a "chilled air source power switch" 16 and a "vacuum suction source power switch" 18. A "chilled air source connective hose port" 20 is located on the top, a "vacuum suction source connective hose port" 22 is located on the bottom.

FIG. 2 shows the top view of a hand held "scalp, hair, and skin, treatment tool". FIG. 2 treatment tool's discussion excludes facial skin treatment which is addressed by FIGS. 3 and 3A, 4 and 4A. The housing should be of a shape and size comfortable to hold and operate. FIG. 2 indicates a "chilled air connective hose port" 26 and a "vacuum suction connective hose port" 28. The view shows two "abrading platform pulse power switches" 24 used to initiate movement of an "abrading accessory attachment platform" 32 (FIG. 2A).

FIG. 2A shows the bottom view of the FIG. 2 treatment tool. The housing includes motorized parts necessary to cause movement of an "abrading accessory attachment platform" 32, located centrally. The assembly shall include proper abrading attachment accessories (not shown) to accommodate scalp treatments, short or long hair treatments, and skin treatments. An opening is displayed on both sides of the abrading platform 32. The first is a "chilled air exhaust vent" 30; the second is a "vacuum suction cavity" 34.

FIG. 3 shows the top view of a hand held "facial skin treatment tool". The housing should be of a shape and size comfortable to hold and operate. The treatment tool's function and design are similar to FIGS. 2 and 2A treatment tool with the omission of the chilled air function. FIGS. 4 and 4A's "chilled air flow funnel" is used in conjunction with FIGS. 3 and 3A treatment tool enabling the tool to be of smaller size for facial applications. A "vacuum suction connective hose port" 38, located centrally, is utilized for this design. The view shows two "abrading platform pulse power switches" 36 used to initiate movement of an "abrading accessory attachment platform" 42 (FIG. 3A).

FIG. 3A shows a bottom view of the FIG. 3 treatment tool. The housing includes motorized parts necessary to cause movement of an "abrading accessory attachment platform" 42. A "vacuum suction cavity" 40 is located in the center of the platform" 42. The assembly shall include proper abrading attachment accessories (not shown) to accommodate facial skin and sensitive areas of skin surrounding the eyes.

FIG. 4 displays the front view of a "chilled air flow funnel" used in conjunction with FIGS. 3 and 3A's treatment tool. Approximately in the center of the funnel is the location of a "chilled air exhaust vent" 44.

FIG. 4A shows the back view of the FIG. 4 funnel. Approximately in the center of the funnel is the location of a "chilled air connective hose port" 46.

FIG. 5 shows a "chilled air connective hose". The hose is expandable and of a length which is neither limiting nor cumbersome. It should be made of a polymer material which is thermally stable at approximately 4° C. The hose's ends 48 are of a connective nature. The hose provides a "dry" chilled air flow from FIG. 1A unit's "chilled air hose connective hose port" 20 to FIG. 2 treatment tool's "chilled air connective hose port" 26 or to FIG. 4A funnel's "chilled air connective hose port" 46.

Figure 6:
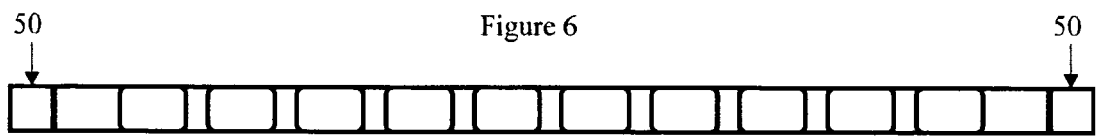
FIG. 6 shows the preferred embodiment of a "vacuum suction connective hose".

FIG. 6 shows a "vacuum suction connective hose". The hose is expandable and of a length which is neither limiting nor cumbersome. It should be made of a polymer material which withstands the necessary vacuum pressure without collapse. The hose's ends 50 are of a connective nature. The hose provides vacuum suction connection from FIG. 1A unit's "vacuum suction source connective hose port" 22 to FIG. 2 treatment tool's "vacuum suction connective hose port" 28 or FIG. 3 treatment tool's "vacuum suction connective hose port" 38.

Connective hoses (FIGS. 5 and 6) may be identical providing their material composition and structure withstand both temperature and vacuum pressure requirements.

Operation—FIGS. 1 TO 6

This paragraph discusses treatment for the scalp, hair, and skin and excludes discussion of facial skin treatment described in the subsequent paragraph. A "chilled air and vacuum suction unit" (FIG. 1) is comprised of a "chilled air source" 10, a "vacuum suction source" 12, and a "waste collection location" 14. The chilled air source 10 provides a dry, chilled air flow to a "scalp, hair, and skin, treatment tool" (FIGS. 2 and 2A). The dry, chilled air flow is delivered by a "chilled air connective hose" (FIG. 5). The hose's connective ends 48 are identical and are inserted into the unit's (FIG. 1A) "chilled air source connective hose port" 20 and the treatment tool's (FIG. 2) "chilled air connective hose port" 26. Chilled air flow power is initiated using the unit's (FIG. 1A) "chilled air source power switch" 16. The dry, chilled air flow exits the tool's (FIG. 2A) "chilled air exhaust vent" 30. The chilled air freezes impurities on the scalp, hair, and skin. The unit's (FIG. 1) "vacuum suction source" 12 supplies suction to the treatment tool's (FIG. 2A) "vacuum suction cavity" 34 via a "vacuum suction connective hose" (FIG. 6). The hose's connective ends 50 are identical and are inserted into the unit's (FIG. 1A) "vacuum suction source connective hose port" 22 and the treatment tool's (FIG. 2) "vacuum suction connective hose port" 28. Vacuum suction power is initiated using the unit's (FIG. 1A) "vacuum suction source power switch" 18. Vacuum suction is employed to remove frozen impurities from the scalp, hair, and skin. The treatment tool's (FIGS. 2 and 2A) housing consists of motorized parts necessary to cause movement of the tool's (FIG. 2A) "abrading accessory attachment platform" 32. Various styles of abrading pads (not shown) shall be made available for attachment to the platform. Abrading pads types shall support the gentle agitation and freeing of frozen impurities from the scalp, hair, and skin. Platform movement is initiated by "abrading platform pulse power switches" 24 (FIG. 2) applied as needed. The functions of cooling, abrading, and vacuum suctioning shall occur simultaneously. The treatment is employed "dry" meaning no use of solutions and perspiration is not encouraged. The treatment area should be clean and dry. Scalp treatment is considered primary, followed by neck and facial skin treatment, and finally remaining bodily skin treatment. The actual scalp and hair treatment consists of first selecting the proper abrading pad attachment and securing it to the tool's (FIG. 2A) abrading platform 32. The activated treatment tool is held against the scalp and slowly moved to all areas, in all directions of the scalp. The abrading platform is activated continuously or on an as needed basis. Treatment tool directions, which produce the greatest effects, will differ due to varying hair patterns. Hair strand treatments are performed in the order of root to end. Skin treatment is performed by holding the skin taut with one hand while moving the activated treatment tool's abrading pad against the skin. As with scalp and hair treatments, most effective movement directions will differ with varying skin patterns.

For facial skin treatment a "chilled air flow funnel" (FIGS. 4 and 4A) is used in conjunction with a "facial skin treatment tool" (FIGS. 3 and 3A). The funnel (FIGS. 4 and 4A) allows the impurity freezing function to operate separately from the treatment tool (FIGS. 3 and 3A). This permits for a smaller, less cumbersome treatment tool for use on facial skin. The dry, chilled air flow is delivered by a "chilled air connective hose" (FIG. 5). The hose's connective ends 48 are identical and are inserted into the unit's (FIG. 1A) "chilled air source connective hose port" 20 and the funnel's (FIG. 4A) "chilled air connective hose port" 46. Chilled air flow power is initiated using the unit's (FIG. 1A) "chilled air source power switch" 16. The "dry" chilled air flow exits the funnel's (FIG. 4) "chilled air exhaust vent" 44. The funnel is positioned on an adjustable stand (not shown) in a position which targets the chilled air flow directly at the face. Chilled air flow shall be administered prior to and throughout the facial skin treatment. The unit's (FIG. 1) "vacuum suction source" 12 supplies suction to the treatment tool's (FIG. 3A) "vacuum suction cavity" 40 via a "vacuum suction connective hose" (FIG. 6). The hose's connective ends 50 are identical and are inserted into the unit's (FIG. 1A) "vacuum suction source connective hose port" 22 and the treatment tool's (FIG. 3) "vacuum suction connective hose port" 38. Vacuum suction power is initiated using the unit's (FIG. 1A) "vacuum suction source power switch" 18. The treatment tool's (FIGS. 3 and 3A) housing consists of motorized parts necessary to cause movement of the tool's (FIG. 3A) "abrading accessory attachment platform" 42. Various styles of abrading pads (not shown) shall be made available for attachment to the platform. Abrading pads types shall support the gentle agitation and freeing of frozen impurities from facial skin. Platform movement is initiated by "abrading platform pulse power switches" 36 (FIG. 3) applied as needed. Facial skin treatments are administered in the same manner as discussed previously for skin treatment.

Summary, Ramifications, and Scope

This technique allows the finding that impurities on the scalp, hair, and skin, freeze at a much higher temperature than that of the healthy skin and scalp tissue. Freezing the impurities renders such impurities in a crystalline state. In a crystalline form the impurities' bond to the scalp, hair, and skin, is lessened considerably allowing for a much greater degree of removal when used in conjunction with abrading and vacuum suction removal.

For added safety, the abrading accessory attachment platforms, seen in FIGS. 2A and 3A, may be designed to cease movement when too much pressure is applied during treatment.

For convenience, a mirror may be attached to the "chilled air flow funnel" (FIGS. 4 and 4A) when performing neck and facial skin treatments.

A less aggressive version of this process may be used to gently remove "cradle cap" from infant's scalp.

This process may be beneficial in the removal of hair and skin impurities from pets. The drawings and accompanying descriptions have shown and described the preferred embodiment of the present impurity removal process. It should be apparent to those skilled in the art that various changes may be made in the form of the invention without affecting the scope of the process. The example given is presented simply to display one form of the process of freezing, freeing, and removing frozen impurities from the scalp, hair, and skin, rather than the mechanical aspects of employing the process.

The invention claimed is:

1. A non-surgical, complete outer body, cleansing device which enables the process of freezing, physically changing, freeing, and removing impurities from living tissue surfaces of the scalp, hair, and skin when employed on dry, cleansed scalp, hair or skin devoid of cosmetic and/or medicinal product, with a device housing being of size and shape comfortable to hold and operate, with a bottom being a treating surface of the device, with the housing comprising:

(a) a top entry port which accepts a connective hose fixed to a chilled air source which when activated directs a dry, solution free, chilled airflow through the connective hose to an exhaust vent or vents, located on the bottom of the device, directly on a surface to be treated at such a temperature as to freeze impurities, without freezing living tissue, to change the shape, crystallinity and size of said impurities, resulting in the skin's pores, lines and wrinkles expulsion of said frozen impurities on, and with edges above, the treated surface; with (b) an abrasion platform, located at the bottom, with internal motorized parts necessary to initiate movement by using on/off or pulse switches located on a housing top, and allows the attachment of an appropriate abrasion accessory needed to accommodate various treatment areas, which gently abrades and agitates the frozen impurities in such a way as to free and separate them from the living tissue of the treated surfaces with the abrasion accessory without removal of dermal layers with the platform agitating gently; with (c) a top entry port which accepts a connective hose fixed to a vacuum source which when activated applies a vacuum suction to an opening or openings in the device bottom sufficient enough to remove frozen impurities without the removal of living tissue through the connective hose to a waste receptacle to prevent their warming and re-bonding with treated surfaces; which said device (d) enables mandatory functions a, b, and c to operate simultaneously in a safe, gentle, painless, effective manner by the average consumer.

2. A non-surgical, complete outer body method of cleansing the scalp, hair, and skin without cosmetic and/or medicinal product comprising the steps of:

directing a dry, solution free, chilled airflow on a surface of one of at least scalp, hair and skin at such a temperature as to freeze impurities, without freezing living tissue;

crystallizing said impurities, resulting in a reduction in bonding of the impurity to the skin's pores, lines and wrinkles;

abrading the frozen impurities in such a way as to free and separate them from the living tissue;

agitating a surface of living tissue to remove the frozen impurities without removal of dermal layers of the living tissue;

applying vacuum suction to the surface to remove only the frozen impurities without the removal of living tissue;

discarding the frozen impurities to a waste receptacle; and performing the preceding steps simultaneously in a safe, gentle, painless, effective manner.

3. The non-surgical, complete outer body method of cleansing the scalp, hair, and skin without cosmetic and/or medicinal product of claim 2 further comprising the step of ceasing agitation if pressure is applied that may damage the living tissue.

4. The non-surgical, complete outer body method of cleansing the scalp, hair, and skin without cosmetic and/or medicinal product of claim 2 further comprising the step of limiting agitation to prevent the warming and re-bonding of the frozen impurity to the living tissue.

5. The non-surgical, complete outer body method of cleansing the scalp, hair, and skin without cosmetic and/or medicinal product of claim 2 further comprising the step of forming an abrasion pad based on the type of living tissue being treated.

6. The non-surgical, complete outer body method of cleansing the scalp, hair, and skin without cosmetic and/or medicinal product of claim 2 further comprising the step of abrading the surface from a root of hair to the end in a linear manner.

7. The non-surgical, complete outer body method of cleansing the scalp, hair, and skin without cosmetic and/or medicinal product of claim 2 further comprising the step of holding the living tissue taut while abrading the surface.

* * * * *